(12) United States Patent
Hammerly

(10) Patent No.: US 6,605,605 B2
(45) Date of Patent: Aug. 12, 2003

(54) ESTROGENIC SUBSTANCES COMBINED WITH CRUCIFEROUS INDOLE COMPOUNDS

(76) Inventor: Milton Hammerly, 17602 Anton Ct., Parker, CO (US) 80134

(*) Notice: Subject to any disclaimer, the term of this patent is extended or adjusted under 35 U.S.C. 154(b) by 0 days.

(21) Appl. No.: 09/991,516

(22) Filed: Nov. 10, 2001

(65) Prior Publication Data

US 2002/0058648 A1 May 16, 2002

Related U.S. Application Data

(60) Provisional application No. 60/246,996, filed on Nov. 13, 2000.

(51) Int. Cl.$^7$ .................. A61K 31/56; A61K 31/405; A61K 31/40
(52) U.S. Cl. ............... 514/178; 514/177; 514/415; 514/408; 514/171; 514/169
(58) Field of Search ................ 514/170, 172, 514/178, 408, 415, 177

(56) References Cited

U.S. PATENT DOCUMENTS

| | | | | |
|---|---|---|---|---|
| 5,948,808 A | | 9/1999 | Safe | 514/415 |
| 6,001,868 A | | 12/1999 | Firestone et al. | 514/415 |
| 6,086,915 A | * | 7/2000 | Zeligs | 424/455 |

* cited by examiner

*Primary Examiner*—Sreeni Padmanabhan
*Assistant Examiner*—S. Jiang
(74) *Attorney, Agent, or Firm*—Christopher J. Whewell

(57) ABSTRACT

Provided herein are medicinal compositions of matter that comprise an estrogenic medication component and a cruciferous indole component (indole 3-carbinol, diindolylmethane, or any derivative thereof. Through use of the compositions of the invention a heretofore unobserved synergy is observed in the treatment of perimenopause, menopause or any other cause of ovarian failure. The invention also provides procedures for administering the composition to a patient who is afflicted with perimenopause, menopause or any other cause of ovarian failure.

8 Claims, No Drawings

ESTROGENIC SUBSTANCES COMBINED WITH CRUCIFEROUS INDOLE COMPOUNDS

This application claims the benefit of U.S. Provisional Application No. 60/246,996 filed Nov. 13, 2000, the entire contents of which are herein incorporated by reference.

TECHNICAL FIELD

This invention relates to medicinal compositions of matter. More particularly, it relates to medicinal compositions of matter which comprise an estrogenic compound in combination with a cruciferous indole compound, including without limitation indole 3-carbinol, diindolylmethane, and including any derivatives of the foregoing. Compositions according to the invention are suitable for administration orally, or by any other conventional means of administration.

BACKGROUND

Estrogen replacement therapy (ERT) is a commonly-used therapeutic strategy in symptoms associated with menopause and perimenopause, in addition to its use in preventing osteoporosis and other degenerative conditions associated with ovarian failure, or relatively low estrogen levels resulting from other causes. ERT is often associated with certain side effects, and a slight increase in the risk of certain types of breast cancer are recognized with its long-term use. Because of both the side effects and the fear of breast cancer, compliance with ERT by patients is notoriously poor. Many different types of estrogen, different doses, and different forms of administration have been developed to help enhance compliance with ERT. Unfortunately none of the existing ERT products adequately address patient concerns of side effects and increased risk of breast cancer. From metabolic pathway and studies in carcinoma, it has been determined that a preponderance of 16-hydroxyestrogen metabolites is generally associated with an increased risk for breast cancer, and that a preponderance of 2-hydroxyestrogen metabolites is generally associated with a decreased risk of breast cancer. Thus, if a material were available which could provide the beneficial effects of the presence of an estrogenic substance in a body having reduced capability to produce its own estrogens while reducing the quantity of 16-hydroxyestrogen metabolites and simultaneously increasing the quantity of 2-hydroxyestrogen metabolites in the patient's bloodstream, such a material and methods for its administration would be a valuable therapeutic aid for improving many patients' quality of life.

A particular class of compounds known as cruciferous indole compounds are known to exist in a wide variety of plant and particularly vegetable matter. These compounds have been shown to alter steroid hormone metabolism in the human organism. In U.S. Pat. No. 5,948,808 methods for treatment of breast cancer are described using indole-3-carbinol, diindolylmethane, and substituted analogs thereof in the capacity of anti-estrogens. U.S. Pat. No. 6,001,868 discloses a method of inhibiting tumor cell growth comprising contacting a target tumor cell with, or administering to an individual in need thereof, an effective amount of an indole-3-carbinol compound or a derivative thereof, wherein said compound is stable in acidic aqueous solution. However, the inhibition is described therein as being limited to estrogen-independent and the "indole-3-carbinol compound" is not indole-3-carbinol, 3,3'-diindolylmethane.

SUMMARY OF THE INVENTION

The present invention is concerned with medicinal compositions useful for estrogen replacement therapy (ERT) of perimenopause, menopause, or any other cause of ovarian failure or condition in which the production of the body's natural hormones are reduced or eliminated. Compositions according to the invention comprise an estrogenic substance component which may include without limitation estrogen; conjugated estrogens; dienestrol; estrone; esterified estrogens; estradiol; estriol; and estropipate; ethinyl estradiol The cruciferous indole component may include without limitation indole 3-carbinol, diindolylmethane, or any derivative of the foregoing, such as 5-methyl-indole-3-carbinol, 5-ethyl-indole-3-carbinol, 5-propyl-indole-3-carbinol, 5-butyl-indole-3-carbinol, 5-pentyl-indole-3-carbinol, 5-methoxy-indole-3-carbinol, 5-ethoxy-indole-3-carbinol, 5-propyloxy-indole-3-carbinol, 5-butyloxy-indole-3-carbinol, 5-amyloxy-indole-3-carbinol, N-methyl-indole-3-carbinol, N-ethyl-indole-3-carbinol, N-propyl-indole-3-carbinol, N-butyl-indole-3-carbinol, N-pentyl-indole-3-carbinol, 2-methyl-indole-3-carbinol, 2-ethyl-indole-3-carbinol, 2-propyl-indole-3-carbinol, 2-butyl-indole-3-carbinol and 2-pentyl-indole-3-carbinol.

The invention is also concerned with a process for treating a human patient who is afflicted with menopause, perimenopause, or any other cause of ovarian failure or reduced hormone levels, which comprises the steps of providing a composition according to the invention and introducing such a composition into such patient's body.

DETAILED DESCRIPTION

The present invention is directed at therapeutically effective compositions of matter which comprise a combination of any estrogenic medication and any cruciferous indole compound(s). According to a preferred form of the invention, such combinations are suitable for oral administration by the patient themselves. In another embodiment, the combination may be administered bucally, dermally, enterally, or parenterally. In addition, compositions according to the invention may be ingested or applied chronically, intermittently, or cyclically for any length of time depending on the preferences of both the patient and the treating physician. Thus, the number of combinations of agents and their embodiments embraced are broad and varied.

ERT Medications

Medications currently available for ERT such as conjugated estrogens (CENESTIN®/PREMARIN®/PREMPRO®/PREMPHASE®), dienestrol (ORTHODIENESTROL®), esterified estrogens (ESTRATAB®/MENEST®/ESTRATEST®), estradiol (ALORA® patches/CLIMARA® patches/FSCLIM® patches/ESTRACE® tabs & cream/ESTRADERM® patches/ESTRING®/VIVELLE® patches/COMBIPATCH®/ORTHO-PREFEST®), estriol (available singly or in combination with other estrogenic compounds through compounding pharmacies) and estropipate (OGEN®/ORTHO-EST®), ethinyl estradiol (ESTINYL®/FEMHRT®) can help reduce symptoms of ovarian failure and prevent osteoporosis but do nothing to prevent estrogenic side effects and the increased risk of breast cancer associated with ERT. Therefore existing medications focus exclusively on estrogen replacement without addressing how estrogen metabolism can be altered to reduce side effects and long-term risks of ERT. Thus, while the abovementioned estrogenic medications can help reduce symptoms of ovarian failure and prevent the onset of osteoporosis, they do nothing to prevent the side-effects of the compounds and their metabolites, and the associated increased risk of breast cancer associated with ERT.

In general terms, the human ovaries excrete two general classes of hormone substances, the estrogens and the progesterones. Estrogenic effects are produced by the body's main estrogenic hormone secretions, estrogen and estradiol. Again, in general terms, the effective dosages of estrogenic substances tend to vary depending upon the specific estrogenic substance under consideration. The more potent estrogenic substances such as ethinyl estradiol and estradiol are effective at dosages as low as about 0.1 milligrams on a daily basis for a patient having a body mass of about 60 kg. Larger doses of the weaker estrogenic substances are required, as is known to those skilled in the pharmaceutical and medical arts. However, the dosages of estrogenic substances are well-known in the art, and are set forth in the Physicians Desk Reference, 2000 edition, the entire contents of which is herein incorporated by reference thereto. For purposes of this specification and the appended claims, the words "estrogenic substance" means any substance or its metabolites in the body which when provided to the bloodstream of a human subject exerts effects which are recognized as estrogenic by those skilled in the medical arts upon bodily tissues with which they come in contact.

Cruciferous Indole Compounds

Cruciferous indole compounds include without limitation indole 3-carbinol, diindolylmethane, and any derivatives of the foregoing. These compounds are believed to enhance estrogen metabolism, and thereby reduce the side effects and long-term risks of ERT. Indole 3-carbinol and diindolylmethane are naturally occurring compounds found in cruciferous vegetables such as bok choy, broccoli, Brussels sprouts, cabbage, cauliflower, kale, kohlrabi, mustard, rutabagas, and turnips. Indole 3-carbinol is a metabolic precursor for diindolylmethane, with two molecules of indole 3-carbinol required to produce one molecule of diindolylmethane. Consumption of cruciferous vegetables is believed by some to be associated epidemiologically with a lower incidence of breast cancer. Both indole 3-carbinol and dindolylmethane are believed to be metabolized by the same enzymatic system used in human cells to metabolize estrogenic compounds. Consumption of indole 3-carbinol or diindolylmethane is believed to cause enzymatic induction that enhances the metabolism of these compounds, as well as the metabolism of estrogenic compounds. The result is a relative increase of 2-hydroxyestrogen metabolites and a relative decrease of 16-hydroxyestrogen metabolites.

In addition to the cruciferous indole compounds, their derivatives are also useful in combinations according to the invention. Such derivatives included without limitation: 5-methyl-indole-3-carbinol, 5-ethyl-indole-3-carbinol, 5-propyl-indole-3-carbinol, 5-butyl-indole-3-carbinol, 5-pentyl-indole-3-carbinol, 5-methoxy-indole-3-carbinol, 5-ethoxy-indole-3-carbinol, 5-propyloxy-indole-3-carbinol, 5-butyloxy-indole-3-carbinol, 5-amyloxy-indole-3-carbinol, N-methyl-indole-3-carbinol, N-ethyl-indole-3-carbinol, N-propyl-indole-3-carbinol, N-propyl-indole-3-carbinol, N-butyl-indole-3-carbinol, N-pentyl-indole-3-carbinol, 2-methyl-indole-3-carbinol, 2-ethyl-indole-3-carbinol, 2-propyl-indole-3-carbinol, 2-butyl-indole-3-carbinol and 2-pentyl-indole-3-carbinol. Thus, for purposes of this specification and the appended claims, the words "derivates" when referring to derivatives of cruciferous indole compounds includes the aforementioned molecules.

According to the invention, combinations are provided which, while the inventor hereof is not to be construed as being bound by any particular theory, are believed to cause the preponderance of 16-hydroxyestrogen and decrease of 2-hydroxyestrogen metabolites caused by the administration of ERT (and generally associated with a decreased risk of breast cancer) to be offset or eliminated by a relative increase of 2-hydroxyestrogen metabolites and accompanied relative decrease of 16-hydroxyestrogen metabolites brought on by the ingestion of indole 3-carbinol or diindolylmethane. Combinations according to the invention which comprise a cruciferous indole compound and estrogenic substances used in ERT complement each other by different, mutually-compatible mechanisms of action. The use of such novel combination to treat patients experiencing menopause, perimenopause or any other cause of ovarian failure is thus believed to reduce side effects and long-term risks of ERT, thereby enhancing patient compliance, and enhancing the overall quality and duration of the lives of those who undergo a therapy using a combination according to the invention.

The optimum dosage levels of the estrogenic component in a combination according to the invention is dependent on the recommended specific dosage for the particular estrogenic material selected, and the relative strength of the specific cruciferous indole compound(s) used. In general, the estrogenic substance component of a composition according to the invention may be present in any amount between 0.005% and 99.5% by weight based upon total weight of the composition, including every thousandth percentage therebetween. The cruciferous indole compound component of a composition according to the invention may be present in any amount between 0.05% and 99.5% by weight based upon total weight of the composition, including every hundredth percentage therebetween.

Compositions according to the invention may be prepared by conventional mixing or cocomminuting the estrogenic substance component and cruciferous indole compound components with one another, as such methods of mixing medicinal substances with one another are known in the art. According to another form of the invention, a suspension in oil of the respective components may be prepared and mixed. According to one preferred form of the invention, an oil suspension containing the components of a composition according to the invention may be contained in a softgel capsule or other capsule, as such preparations are known to those in the pharmaceutical arts. In cases where it is desired to provide a combination according to the invention in the form of a tablet or pill, various binders and carriers, the use of which are well-known to those skilled in the art, may be included in the inventive combinations.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

I claim:

1. A single-dose medicament useful in estrogen replacement therapy comprising a composition comprising:
   a) an estrogenic substance; and
   b) a cruciferous indole compound,
   wherein said estrogenic substance is selected from the group consisting of: estrogen; conjugated estrogens;

dienestrol; estrone; esterified estrogens; estradiol; estriol; estropipate; and ethinyl estradiol, and wherein the quantity of said cruciferous indole compound component is at least 0.5 milligrams.

2. A composition as set forth in claim 1 wherein said cruciferous indole compound is selected from the group consisting of: indole 3-carbinol, diindolylmethane, 5-methyl-indole-3-carbinol, 5-ethyl-indole-3-carbinol, 5-propyl-indole-3-carbinol, 5-butyl-indole-3-carbinol, 5-pentyl-indole-3-carbinol, 5-methoxy-indole-3-carbinol, 5-ethoxy-indole-3-carbinol, 5-propyloxy-indole-3-carbinol, 5-butyloxy-indole-3-carbinol, 5-amyloxy-indole-3-carbinol, N-methyl-indole-3-carbinol, N-ethyl-indole-3-carbinol, N-propyl-indole-3-carbinol, N-butyl-indole-3-carbinol, N-pentyl-indole-3-carbinol, 2-methyl-indole-3-carbinol, 2-ethyl-indole-3-carbinol, 2-propyl-indole-3-carbinol, 2-butyl-indole-3-carbinol and 2-pentyl-indole-3-carbinol.

3. A composition according to claim 1 wherein said estrogenic substance component is present in any amount between 0.005% and 99.5% by weight based upon the total weight of the composition.

4. A composition according to claim 1 wherein said cruciferous indole component is present in any amount between 0.005% and 99.5% by weight based upon the total weight of the composition.

5. A single-dose medicament according to claim 1 wherein said cruciferous indole compound is indole 3-carbinol.

6. A single-dose medicament according to claim 1 wherein said cruciferous indole compound is diindolylmethane.

7. A single-dose medicament useful in estrogen replacement therapy comprising a composition comprising:
   a) an estrogenic substance; and
   b) a cruciferous indole compound,
   wherein said estrogenic substance is selected from the group consisting of: estrogen; conjugated estrogens; dienestrol; estrone; esterified estrogens; estradiol; estriol; estropipate; and ethinyl estradiol, said estrogenic substance being present in any quantity of between 0.10 milligrams and 50 milligrams, and wherein the quantity said cruciferous indole compound component is selected from the group consisting of: indole-3-carbinol and diindolylmethane, and wherein said cruciferous indole compound component is present in any amount of between 0.5 and 300 milligrams.

8. A single-dose medicament useful in estrogen replacement therapy comprising a composition comprising:
   a) an estrogenic substance; and
   b) a cruciferous indole compound,
   wherein said estrogenic substance is selected from the group consisting of: estrogen; conjugated estrogens; dienestrol; estrone; esterified estrogens; estradiol; estriol; estropipate; and ethinyl estradiol, and wherein said estrogenic substance is present in any quantity of between 0.10 milligrams and 50 milligrams, and wherein the quantity of said cruciferous indole compound component is present in an amount of at least 0.5 milligrams.

* * * * *